US005885932A

United States Patent [19]
Parr et al.

[11] Patent Number: 5,885,932
[45] Date of Patent: Mar. 23, 1999

[54] ACTIVITY PROMOTING ADDITIVES FOR REST-BREAKING AGENTS

[75] Inventors: William John Ernest Parr, Deventer; Robert Jan Butselaar, Hilversum, both of Netherlands; Michael Shaun North, Durban, South Africa

[73] Assignee: Akzo Nobel N.V., Arnhem, Netherlands

[21] Appl. No.: 765,330

[22] PCT Filed: Jul. 3, 1995

[86] PCT No.: PCT/EP95/02575

§ 371 Date: May 28, 1997

§ 102(e) Date: May 28, 1997

[87] PCT Pub. No.: WO96/01049

PCT Pub. Date: Jan. 18, 1996

[51] Int. Cl.$^6$ .......................... A01N 25/30; A01N 33/12; A01N 33/08

[52] U.S. Cl. ............................................................ 504/116

[58] Field of Search ............................................. 504/116

[56] References Cited

U.S. PATENT DOCUMENTS

| | | | |
|---|---|---|---|
| 4,487,625 | 12/1984 | Rieder | 71/77 |
| 4,525,200 | 6/1985 | Kimpara et al. | 71/76 |
| 4,556,410 | 12/1985 | Ronning et al. | 71/78 |
| 5,693,591 | 12/1997 | North et al. | 504/116 |

FOREIGN PATENT DOCUMENTS

| | | |
|---|---|---|
| 0 232 755 | 8/1987 | European Pat. Off. . |
| 0 257 686 | 3/1988 | European Pat. Off. . |
| 0 272 542 | 6/1988 | European Pat. Off. . |
| 0 463 241 | 1/1992 | European Pat. Off. . |
| 2 257 044 | 1/1993 | United Kingdom . |

OTHER PUBLICATIONS

Coggins et al. "Possible Methods to Increase Efficacy of Gibberellic Acid Applied to Navel Orange Trees" Chapter 55 in Adjuvants for Agrochemicals, Chester L. Foy, ed. CRC Press. p. 567–572, 1992.

Blommeart, K.L., "Winter Dormancy and Delayed Foliation", The Deciduous Fruit Grower, (1956) pp. 1–4.

Improved Methods for Breaking Rest in the Peach and Other Deciduous Fruit Species, J. Amer. Soc. 96(94):519–522 1971.

Chemical Dormancy Breaking of Red Raspberry, Hort-Science 18(5):710–713 1983.

Effect of cyanamide and DNOC/oil on budbreak, yield and fruit size of Golden Delicious apples, S. Afr. Tydskr.Plant Ground 1989, 6(3).

Artificial Rest–Breaking of Apricot and Plum Cultivars Using Hydrogen Cynamide, J.S.Afr.Soc.Hort.Sci., 1.(1) May 1991.

Overcoming rest at different growth stages with hydrogen cynamide, Scientia Horticultuae, 50 (1992) 107–113.

Alternative rest–breaking agents to DNOC/oil for apples, S.Afr.J. Plant Soil 1992 9(1).

Effects of autumnal nitrogen nutrition, urea sprays and a winter rest–breaking spray on budbreak and blosssming of young Golden Delicious trees grown in sand culture, The Deciduous Fruit Grower, Jan. 1973.

Time of Thirourea–$KNO_3$ Application on the Rest Requirement and Bud Developement in "Loring" Peach, Hort-Science, vol. 11(4), Aug. 1976.

Chemical treatments for breaking rest in peach in relation to accumulated chilling, Journal of Horticultural Science (1987) 62 (4) 457–461.

Chemical Abstracts, vol. 118, No.15, 1993, abstract No. 141787.

Chemical Abstracts, vol. 117, No. 1, 1992, abstract No. 2721.

Dormancy Release in Deciduous Fruit Trees, Horticultural Reviews, vol. 7, 1985.

Database WPI, Week 9418, Derwent Publication Ltd.; AN 94–151677, 1994.

English Language Abstract for EP 0 272 542.

Primary Examiner—S. Mark Clardy
Attorney, Agent, or Firm—Ralph J. Mancini

[57] ABSTRACT

Activity promoting additives for rest-breaking agents are disclosed. Further, restbreaking compositions comprising these additives and a rest-breaking agent are also disclosed. Finally, a process for breaking the rest of bushes, shrubs, vines, nuts, berries and non-deciduous fruit trees is disclosed. The activity promoting additives enhance the activity of rest-breaking agents thereby leading to improvements in the yields and quality of fruit, nuts and berries in regions which have mild winter weather conditions.

11 Claims, No Drawings

ACTIVITY PROMOTING ADDITIVES FOR REST-BREAKING AGENTS

This application has been filed under 35 USC 371 as the national phase of international application PCT/EP95/02575, filed Jul., 3, 1995, which claims benefit of priority under 35 U.S.C § 120 of U.S. application Ser. No. 08/270,857 filed Jul. 5, 1994, abandoned.

The present invention relates to the use of particular compounds as activity promoting additives for rest-breaking agents, to rest-breaking compositions comprising these additives and to the use of these compositions for rest-breaking of bushes, shrubs, vines, nuts, berries and non-deciduous fruit trees.

BACKGROUND OF THE INVENTION

Fruit and nut trees, as well as bushes, shrubs, vines and berries, require winter chilling to grow normally. The amount of chilling required depends upon the kind of fruit and the cultivar. If winter chilling is insufficient, then growth abnormalities such as delayed and uneven blossoming, poor leaf cover, insufficient fruit-set and reduced fruit size can occur. These symptoms are generally referred to as delayed foliation according to the article, Blommaert, K. L. J., "Winter Dormancy and Delayed Foliation," *The Deciduous Fruit Grower*, (1956).

Measures to reduce the symptoms of delayed foliation include treatment with high volumes of chemical rest-breaking agents during later winter and various physical manipulations such as pruning.

In South Africa, for example, most apple trees receive insufficient winter chilling to break rest completely and thus annual application of a chemical rest-breaking agent is standard practice. The most widely used rest-breaking agent in commercial apple orchards is dinitro-ortho-cresol (DNOC) in combination with winter-oil emulsion (a lipophilic agent) (Erez, A. et al., "Improved Methods of Breaking Rest in the Peach and Other Deciduous Fruit Species," *J. Amer. Soc. Hort. Sci.*, 96, pp. 519–522 (1971)). This article also mentions the use of the potassium salt of gibberellic acid, kinetin, indoleacetic acid and thiourea as potential rest-breaking agents.

DNOC is a non-systemic stomach poison and contact insecticide, ovicidal to the eggs of certain insects. It is strongly phytotoxic and its permissable use as an insecticide is limited to dormant sprays or on waste ground. Further, DNOC is known to act as a cumulative poison in man. Although DNOC is relatively inexpensive and effective as a rest-breaking agent, it is toxic enough to limit its continued use and it is currently on the European Red List of agricultural chemicals which will be prohibited in the future. DNOC is also banned in the United States for use as an agricultural chemical.

One of the most effective alternatives to DNOC is hydrogen cyanamide according to the publications, Snir, I., "Chemical Dormancy Breaking of Red Raspberry," *HortScience*, 18, pp. 719–713 (1983); North, M. S., "Effects of Cyanamide and DNOC/oil on Budbreak, Yield and Fruit Size of Golden Delicious Apples," *S. Afr. J. Plant Soil*, 6(3), pp. 176–178 (1989); Stadler, J. D., North, M. S. and Lutze, G. F. A., "Artificial Rest-Breaking of Apricot and Plum Cultivars Using Hydrogen Cyanamide," *J.S.Afr.Soc.Hort.Sci.*, 1(1), pp. 9–11, (1991); Nee, C. C. and Fuchigami, L. H., "Overcoming Rest at Different Growth with Hydrogen Cyanimide," *Scientia Horticulturae*, 50, pp. 107–113 (1992); and North, M. S., "Alternative Rest-Breaking Agents to DNOC/oil for Apples," *S. Afr. J. Plant Soil*, 9(1), pp. 39–40 (1992).

Hydrogen cyanamide is a skin and eye irritant and is especially acute when used in combination with the consumption of alcohol. The toxicity and relatively high price limit its market acceptance and hydrogen cyanamide has also been placed on the European Red List.

Thus, there exists an immediate need for new, milder rest-breaking agents, not only in South Africa, but also in countries which are currently developing agricultural industries but do not have an ideal climate therefor, such as Brazil. Further, there is a need for such new rest-breaking agents in countries with existing agricultural industries that, up to now, did not appreciate the extent of the problem of delayed foliation.

The response of a plant to a rest-breaking agent is dependent upon the chemical composition of the agent, its application rate and timing and on the nutritional status of the plant according to Terblanche, J. H. and Strydom, D. K., "Effects of Autumnal Nitrogen Nutrition, Urea Sprays and a Winter Rest-Breaking Spray on Budbreak and Blossoming of Young 'Golden Delicious" Trees Grown in Sand Culture," *Deciduous Fruit Grower*, 23 pp. 8–14 (1973).

Many chemicals have been found to have rest-breaking ability. A summary of some of these chemicals can be found in Saure, M. C., "Dormancy Release in Deciduous Fruit Trees," Janick, J. (Ed.), *Horticultural Reviews*, 7, pp. 239–287, AVI Publishing Co. Inc., Westport, Conn. (1985). The efficacy of these various rest-breaking agents appears to be directly related to their physiological harshness.

One of the milder rest-breaking agents is potassium nitrate which has been shown to have a positive effect on peaches. Generally, fruit trees having a lower chill requirement, such as peaches, also require lower concentrations of rest-breaking agents, whereas fruits with a higher chill requirement, such as apples, require excessive concentrations of a mild rest-breaking agent. Articles demonstrating the effects of thiourea, potassium nitrate and combinations thereof include, Wolak, R. J. and Couvillon, G. A., "Time of Thiourea-KNO$_3$ Application on the Rest Requirement and Bud Development in 'Loring' Peach," *HortScience*, 11(4), pp. 400–402, (1976) and Fernandez-Escobar, R. and Martin, R., "Chemical Treatments for Breaking Rest in Peach in Relation to Accumulated Chilling," *J. Hort. Sci.*, 62(4), pp. 457–461, (1987).

For the foregoing reasons, there exists a need in the art for improved rest-breaking agents which are, affordable, effective, less toxic than the present rest-breaking agents and which can be employed in reasonable concentrations.

SUMMARY OF THE INVENTION

The present invention relates to a process for enhancing the rest-breaking in bushes, shrubs, vines, nuts, berries and non-deciduous fruit trees which comprises the step of applying to at least one of these plants, before blossom, an effective amount of at least one rest-breaking agent and a compound selected from the group consisting of alkoxylated amines represented by the following general formula:

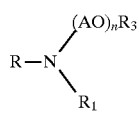

wherein n is an integer from 1 to 50, A represents an alkylene group and when n>1, each A may be the same or different alkylene groups, R is selected from straight or branched chain alkyl or alkenyl groups having 8 to 22 carbon atoms and groups represented by the formula:

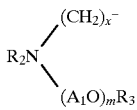

wherein m is an integer from 1–50, $A_1$ represents an alkylene group and when n>1, each $A_1$ may be the same or different alkylene groups, x is an integer from 1–6, and $R_2$ is selected from straight or branched chain alkyl or alkenyl groups having 8 to 22 carbon atoms, $R_3$ is selected from hydrogen, 1–8 carbon atom straight or branched chain alkyl and alkenyl groups and aryl groups having up to 8 carbon atoms; and $R_1$ is selected from hydrogen, straight or branched chain alkyl and alkenyl groups having 1–22 carbon atoms, a group represented by the formula:

wherein n' is an integer from 1 to 50 and $A_2$ represents an alkylene group and when n'>1 each $A_2$ may be the same or different alkylene groups; and alkoxylated quaternary ammonium compounds represented by the following general formula:

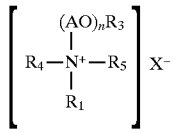

wherein n, A, $R_1$ and $R_3$ are as defined above, X is an anion, $R_5$ is selected from hydrogen, straight or branched chain alkyl or alkenyl groups having 1 to 4 carbon atoms, and benzyl, or $R_5X$— is carboxymethyl as in betaines or oxygen as in amine oxides; $R_4$ is selected from straight or branched chain alkyl and alkenyl groups having 8–22 carbon atoms and groups represented by the formula:

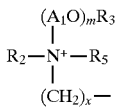

wherein $A_1$, m, $R_2$, $R_3$, $R_5$ and x are as defined above.

More particularly, X may be halides such as $Cl^-$, $Br^-$, $CH_3SO_4^-$, and $C_2H_5SO_4^-$, among others. The anion associated with these quaternary ammonium compounds is not critical to the process of the present invention.

These compounds are known from European patent application publication number 0 463 241 where it is disclosed that these compounds are useful as blossom thinning agents for stone fruits. In addition, a small group of the foregoing compounds are known from European patent 0 257 686 which discloses several alkoxylated amines and their use as activity promoting additives for herbicides and fungicides. Also disclosed therein is a method for making these compounds, which method is hereby incorporated by reference.

As a result of extensive research it has now been found that the above-identified compounds can be used as adjuvants for chemical rest-breaking agents for plants. These compounds exhibit a substantial effect when combined with rest-breaking agents, and human toxicity and phytotoxicity studies have shown that these compounds have acceptably low levels of toxicity to humans and other plants. Further, the compounds do not cause significant harm to useful insect populations. Finally, the activity-enhancing effect of these compounds allows the use of milder rest-breaking agents which are less toxic, as well as the use of lower concentrations of rest-breaking agents.

The amino compounds of the present invention may be prepared by reacting an amine selected from the group consisting of R—$NH_2$, RRNH, and R—NH—(($CH_2$)$_x$—NH)$_n$R' wherein R and R' are aliphatic hydrocarbon groups having 8–22 carbon atoms, n=1–5 and x is an integer from 1–6; with at least one alkylene oxide.

The preferred alkylene oxides for use in the present invention are ethylene oxide, propylene oxide, isobutylene oxide and butylene oxide. The compounds of the present invention are made in such a way as to introduce varying numbers of alkylene oxide units onto the amino nitrogen. Thus, these alkylene oxide groups may be all the same, such as, for example, one or more ethylene oxide units, or the groups may be different to form, for example, block copolymer chains of ethylene oxide and propylene oxide units, random copolymer chains consisting of several units of each of two or more different alkylene oxides, or alternating units of two or more alkylene oxides. Any conceivable combination of alkylene oxide units up to 50 units long may be employed at each location on the amino nitrogen which is to contain such units. In addition, a single amino nitrogen may contain two different alkylene oxide chains attached thereto or two chains which are the same.

In the most preferred embodiments of the present invention, block copolymer chains of ethylene oxide and one or more of propylene oxide or butylene oxide are employed. Preferably, the molar weight of the compounds used in the present invention is less than 8000 though higher molecular weight compounds can be employed in some circumstances.

The amino compounds can also be quaternized by known quaternization methods to produce quaternary ammonium compounds which are also useful in the process of the present invention. The fourth substituent added to the amino nitrogen by quaternization may be an alkyl, aryl or alkenyl group having 1 to 4 carbon atoms. The anion associated with such quaternary ammonium compounds is not critical to the process of the present invention.

Typical compounds suitable for use in the process of the present invention include, but are not limited to, cocobis (2-hydroxyethyl)methylammonium chloride, polyoxyethylene (15) cocomethylammonium chloride, oleylbis (2-hydroxyethyl)methylammonium chloride, polyoxyethylene (15) stearylmethylammonium chloride, cocobis (2-hydroxyethyl)amine, polyoxyethylene(5)cocoamine, polyoxyethylene(15)cocoamine, tallowbis (2-hydroxyethyl) amine, polyoxyethylene(5)tallowamine, polyoxyethylene (15)tallowamine, tallow/oleylbis(2-hydroxyethyl)amine, oleylbis(2-hydroxyethyl)amine, polyoxyethylene(5) oleylamine, polyoxyethylene(15)oleylamine, hydrogenated tallowbis(2-hydroxyethyl)amine, hydrogenated polyoxyethylene(5)tallowamine, hydrogenated polyoxyethylene(15)tallowamine, hydrogenated polyoxyethylene(50)tallowamine, N,N',N'-tris(2-hydroxyethyl)-N-tallow-1,3-diaminopropane, N,N',N'-polyoxyethylene(10)-N-tallow-1,3-diaminopropane, and N,N',N'-polyoxyethylene(15)-N-tallow-1,3-diaminopropane.

The process of the present invention is useful for rest-breaking of bushes, shrubs, vines, nuts, berries and non-deciduous fruit trees to produce improvements advancing the time of bloom, budbreak and/or leaf cover and fruit set.

The present process also enables the use of either milder rest-breaking agents or smaller quantities of harsher rest-breaking agents thus providing considerable advantages in toxicity to man and insect populations as well as safety advantages in the application of these agents.

Examples of the types of plants to which the present invention is applicable are grape vines, olive trees, raspberries, strawberries, cranberries, blackberries, loganberries, blackcurrants, redcurrants and any non-deciduous fruit trees. Nuts include, but are not limited to, almonds, walnuts and chestnuts.

When reference is made in this patent application to enhancement of rest-breaking, what is meant is that the time of bloom is advanced or one or more budbreak and/or leaf cover or fruit set are improved over a control tree.

The process of the present invention is to be applied to the respective plants, prior to blossom. The process is particularly useful in growing areas where the winter chilling of the plants is insufficient to provide good budbreak and fruit set for the particular cultivar. Winter chilling can be measured and is often represented by the unit, "Richardson Chill Units."

The optimum time to break rest for a particular plant will depend upon several factors including the type of fruit, the cultivar, the climatic conditions and the type and amount of rest-breaking agent being applied. For some fruit or cultivar species, the best rest-breaking effects are accomplished by early application of the rest-breaking agent to the plants whereas for others it is best to wait until just before blossom. In general, the rest-breaking agent will be applied at some point between the time when winter has peaked and the time when blossoming begins.

One of the effects of the rest-breaking agents of the present invention is to accelerate the blossoming of the plants. Accordingly, in the application of these rest-breaking agents consideration should be given to this effect and the agents should not be applied too early such that blooming occurs when there is still a risk of harsh weather.

The process of the present invention is carried out by the application of an effective amount of at least one rest-breaking agent in combination with an amount of at least one compound as defined herein to enhance the rest-breaking activity of said rest-breaking agent. The rest-breaking compositions are preferably applied in the form of an aqueous solution in a concentration of 0.25 to 30% and more preferably from 0.5 to 10%. The lower limit is generally determined by the upper limit on application volume for the particular application equipment being employed, as well as by the type of fruit, the cultivar and the particular rest-breaking composition.

The upper concentration limit will generally be dictated by phytotoxicity considerations since higher concentrations of certain compounds have a localized phytotoxic effect on the trees. Thus, a concentration should be selected which provides adequate rest-breaking without unwanted phytotoxic effects on the remainder of the plant. Such concentrations can be selected by routine experimentation with the particular species of plant.

The activity promoting additive of the present invention is generally employed in a concentration of 0.1–10.0% in the aqueous solution and more preferably, 0.2–5.0%. Again, the amount of activity promoting additive required will depend on the fruit, the cultivar and the particular rest-breaking agent, as well as the quantity of rest-breaking agent to be employed.

Rest-breaking agents which may be used in the process and composition of the invention include any known rest-breaking agent. Examples include hydrogen cyanamide, calcium ammonium nitrate, urea ammonium nitrate, potassium nitrate, the potassium salt of gibberellic acid, kinetin, indoleacetic acid, thiourea, and combinations thereof. The most preferred rest-breaking agents for use in the present invention are calcium ammonium nitrate and urea ammonium nitrate, especially when used on grapes. Also preferred is potassium nitrate. These nitrates are milder agents for which the activity can be enhanced to the desired level by the adjuvants of the present invention.

The composition is preferably applied in a manner similar to the manner in which commercial insecticides are applied. More particularly, conventional equipment such as knapsack sprayers, hand held spray guns, mist blowers, and aerial spraying equipment among others may be used. The composition is applied the same way as in pesticide application. The compositions may also be applied directly to the plant by hand, if desired.

The process of the present invention has the significant advantages that it breaks rest to the extent that the use of known, highly toxic rest-breaking agents can be eliminated or considerably reduced, it can be done in a manner which is safe for the crops and the treatment has no long term phytotoxic effect on the plants, if carried out correctly. Further, the rest-breaking process will cause significantly less harm to beneficial insects when applied within the normal application volume, and the process appears to be environmentally acceptable, non-hazardous to operators of the application equipment, and non-corrosive to the equipment.

The present invention will be further illustrated by the examples appended hereto.

EXAMPLES 1–12 AND COMPARATIVE EXAMPLES A–C

Effect of Armobreak™ adjuvant used with Dormex™ Rest-Breaking Agent on the Perlette Table Grape In Examples 1–12, various combinations of Dormex™ (hydrogen cyanamide rest breaking agent) and Armobreak™ (activity promoting additive) in aqueous spray solutions were employed as rest-breaking agents in Perlette grapes. These tests were carried out in the Coachella Valley of California with, as the purpose, to overcome the effects of inadequate winter chilling.

These examples were conducted in a commercial Perlette table grape vineyard located near Thermal, Calif. The own-rooted vines were planted 12 feet apart between rows and 6 feet apart between vines and were cordon trained and spur pruned. The vines were drip irrigated. The vines were pruned to 40, two-bud spurs on 15 Dec. The experimental treatments of the present examples were applied the following day.

Each treatment was replicated eight times using single vine plots. The treatments were arranged in a randomized complete block, split-plot design. A single vine served as a buffer between each plot.

The treatments of all the field trials in the examples have all been applied by a hand held spray wand at the rate of 100 gallons of spray solution per acre. The vines were monitored two to three times per week to determine the rate of bud emergence. The date of shoot emergence was recorded for the buds of ten randomly selected spurs on each vine.

Armobreak™ which is a tallowamine containing fives moles of ethylene oxide derived units and a total of 12 moles of propylene oxide units, can be represented by the general formula:

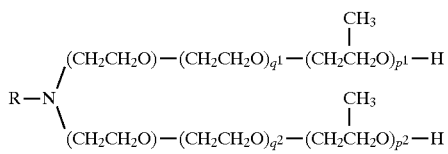

wherein (p1+p2)=12, (q1+q2)=3 and R is a hydrocarbon group derived from tallow fatty acid.

Comparative Examples A–C are the control examples where only Dormex™ was applied.

Results:

The following Table I gives the results obtained in these examples. All amounts are volume percent, based on the total volume of the aqueous solution.

The results for budbreak represent the number of days required to reach 70% of the total budbreak for a given grapevine.

TABLE 1

| Example | Dormex ™ (% v/v) | Armobreak ™ (% v/v) | Days Until 70% Budbreak |
|---------|------------------|---------------------|-------------------------|
| A | 1.0 | 0.0 | 58 |
| B | 2.0 | 0.0 | 47 |
| C | 4.0 | 0.0 | 42 |
| 1 | 1.0 | 0.5 | 48 |
| 2 | 2.0 | 0.5 | 37 |
| 3 | 4.0 | 0.5 | 35 |
| 4 | 1.0 | 1.0 | 42 |
| 5 | 2.0 | 1.0 | 34 |
| 6 | 4.0 | 1.0 | 36 |
| 7 | 1.0 | 2.0 | 38 |
| 8 | 2.0 | 2.0 | 34 |
| 9 | 4.0 | 2.0 | 36 |
| 10 | 1.0 | 3.0 | 36 |
| 11 | 2.0 | 3.0 | 33 |
| 12 | 4.0 | 3.0 | 33 |

These results demonstrate that using 1.0% Dormex™ in combination with 1.0% Armobreak™ gives the same result (42 days) as is obtained using 4.0% Dormex™ without Armobreak™. Thus, the amount of rest-breaking agent can be reduced by up to 75% when employing the Armobreak™ adjuvant of the present invention without compromising the effects obtained with the rest-breaking agent.

EXAMPLES 13–18 and COMPARATIVE EXAMPLES D–L

Effect of Armobreak™ adjuvant used with Dormex™ Rest-Breaking Agent on different varieties of Table Grapes This example illustrates that the ability of Armobreak to act effectively as an adjuvant for the rest breaking agent Dormex™ is general across different varieties of vines. The results are shown in Table 2.

TABLE 2

| Example | Variety | Dormex ™ % (v/v) | Armobreak ™ % (v/v) | % Budbreak 55 days after application |
|---------|---------|------------------|---------------------|--------------------------------------|
| D | Thompson | 1 | 0 | 12 |
| E | Seedless | 2 | 0 | 28 |
| F |  | 4 | 0 | 43 |
| 13 |  | 1 | 2 | 33 |
| 14 |  | 2 | 2 | 44 |
| G | Black | 1 | 0 | 13 |
| H | Seedless | 2 | 0 | 29 |
| I |  | 4 | 0 | 36 |
| 15 |  | 1 | 2 | 37 |

TABLE 2-continued

| Example | Variety | Dormex ™ % (v/v) | Armobreak ™ % (v/v) | % Budbreak 55 days after application |
|---------|---------|------------------|---------------------|--------------------------------------|
| 16 |  | 2 | 2 | 31 |
| J | Red Globe | 1 | 0 | 17 |
| K |  | 2 | 0 | 23 |
| L |  | 4 | 0 | 34 |
| 17 |  | 1 | 2 | 38 |
| 18 |  | 2 | 2 | 39 |

The results show that the addition of 2% Armobreak to Dormex™ rest breaking agent allows equal or better advance of budbreak to be attained at a given time as when using two to four times the concentration of Dormex™ alone, and that this effect is common across different varieties of table grapevines.

EXAMPLES 19–28 AND COMPARATIVE EXAMPLES M–N

Effect of Armobreak™ adjuvant used with Nitrate Rest-Breaking Agents on Perlette Table Grapes The following examples illustrate the utility of Armobreak™ when used with a variety of nitrate rest breaking agents applied to Perlette variety grapevines. The results are shown in Table 3.

TABLE 3

| | | | | Days to reach | |
|---|---|---|---|---|---|
| | Rest breaking agent | | Armobreak ™ | 70% | 90% |
| Example | Name | % | % (v/v) | budbreak | |
| M | — | — | — | 50 | 53 |
| N | Dormex ™ | 4 | — | 33 | 40 |
| 19 | NH$_4$NO$_3$ | 25 | — | 52 | 55 |
| 20 | NH$_4$NO$_3$ | 25 | 2 | 48 | 51 |
| 21 | KNO$_3$ | 15 | — | 53 | 56 |
| 22 | KNO$_3$ | 15 | 2 | 43 | 47 |
| 23 | CaNO$_3$ | 15 | — | 52 | 57 |
| 24 | CaNO$_3$ | 15 | 2 | 43 | 47 |
| 25 | UAN32* | 25 | — | 52 | 58 |
| 26 | UAN32* | 25 | 2 | 37 | 46 |
| 27 | CAN17* | 25 | — | 50 | 55 |
| 28 | CAN17* | 25 | 2 | 33 | 38 |

*UAN32 is a commercially available solution of urea ammonium nitrate; CAN17 is a commercially available solution of calcium ammonium nitrate.

The use of nitrates alone, at the concentrations employed, causes little advance in budbreak relative to control (Example M). The addition of 2% Armobreak causes an improvement in the advance of budbreak with all nitrates tested. However, particular nitrates combined with 2% Armobreak can provide especially large improvements in advance of budbreak. Thus Calcium ammonium nitrate/Armobreak (Example 28) can be seen to provide equal advance of budbreak to the use of 4% Dormex alone (Example N). The combination of Armobreak with urea ammonium nitrate (Example 26) also effects a large advance of budbreak, and the combination of Armobreak with potassium or calcium nitrates also provides some improvement in advance of budbreak relative to the control. The CAN17/Armobreak combination is particularly preferred for use on grapevines.

EXAMPLES 29–32 AND COMPARATIVE EXAMPLE M (CONTROL)

Effect of varying the concentration of Calcium Ammonium Nitrate as a Rest-Breaking Agent on Perlette Table Grapes The following examples demonstrate the effect of varying the concentration of calcium ammonium nitrate used as a rest breaking agent in an experiment conducted on Perlette variety grapevines. The results are shown in Table 4.

TABLE 4

| Example | CAN17 % (v/v) | Armobreak ™ % (v/v) | Days to reach 70% Budbreak | 90% Budbreak |
|---|---|---|---|---|
| M | — | — | 50 | 53 |
| 29 | 10 | — | 50 | 53 |
| 27 | 25 | — | 50 | 55 |
| 30 | 50 | — | 46 | 50 |
| 31 | 10 | 2 | 37 | 46 |
| 28 | 25 | 2 | 33 | 38 |
| 32 | 50 | 2 | 42 | 51 |

It can be seen that in the absence of Armobreak very high concentrations of CAN17 are required to produce effects upon advance of budbreak. In contrast, when 2% Armobreak is added lower concentrations of CAN17 produce considerably larger advances in budbreak. The optimum advance of budbreak produced by CAN17/Armobreak combination can be seen to depend upon the CAN17 concentration.

EXAMPLES 33–34 AND COMPARATIVE EXAMPLE O (CONTROL)

Effect of Armobreak™ adjuvant used with Potassium Nitrate Rest-Breaking agent on Kiwi Fruit The following table shows the effect of Armobreak™, used with potassium nitrate dormancy breaking agent, upon budbreak of kiwi fruit vines. The data are from an experiment in which the treatment solutions were applied to dormant vines about 6 weeks prior to anticipated budbreak, at a solution spray volume of 1600 l/ha. In kiwi fruit it is desirable that any budbreaking treatment also reduce the number of side flowers so as to avoid excessive hand labour. The results are shown in Table 5.

TABLE 5

| Example | Rest Breaking Name | % | Armo-break ™ | Budbreak Total % | 75 days Floral % | Side flowers |
|---|---|---|---|---|---|---|
| 0 | — | — | — | 36.2 | 26.4 | 13.3 |
| 33 | KNO$_3$ | 4 | — | 33.8 | 26.1 | 10.2 |
| 34 | KNO$_3$ | 4 | 2 | 38.5 | 31.6 | 7.4 |

It can be seen that Armobreak enhances the effect of potassium nitrate upon budbreak, and upon the reduction of undesirable side flowers.

The foregoing examples have been presented for purposes of illustration and description only and are not to be construed as limiting the scope of the invention in any manner. Accordingly, the scope of the invention is to be determined by the claims appended hereto.

What is claimed is:

1. A process for enhancing the rest-breaking of plants which comprises the step of applying to at least one plant selected from bushes, shrubs, vines, nuts, berries and non-deciduous fruit trees before blossom, an effective amount of at least one rest-breaking agent and 0.1 to 10% of a compound selected from alkoxylated amines represented by the following general formula:

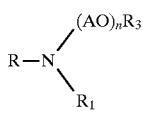

wherein n is an integer from 1 to 50, A represents an alkylene group and when n>1, each A may be the same or different alkylene groups, R is selected from straight or branched chain alkyl or alkenyl groups having 8 to 22 carbon atoms and groups represented by the formula:

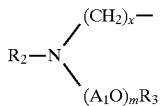

wherein m is an integer from 1–50, $A_1$ represents an alkylene group and when m>1, each $A_1$ may be the same or different alkylene groups, x is an integer from 1–6, and $R_2$ is independently selected from the same groups as R, $R_3$ is selected from hydrogen, straight or branched chain alkyl and alkenyl groups having from 1–8 carbon atoms and aryl groups having up to 8 carbon atoms; and $R_1$ is selected from hydrogen, straight or branched chain alkyl and alkenyl groups having 1–22 carbon atoms, or a group represented by the formula:

wherein n' is an integer from 1 to 50 and $A_2$ represents an alkylene group and when n'>1 each $A_2$ may be the same or different alkylene groups; and alkoxylated quaternary ammonium compounds represented by the following general formula:

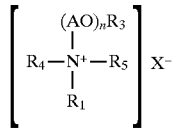

wherein n, A, $R_1$ and $R_3$ are as defined above, X is an anion, $R_5$ is selected from hydrogen, straight or branched chain alkyl or alkenyl groups having 1 to 4 carbon atoms, and benzyl or $R_5X$ is carboxymethyl or oxygen; $R_4$ is selected from straight or branched chain alkyl and alkenyl groups having 8–22 carbon atoms and groups represented by the formula:

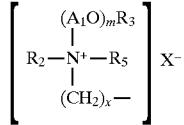

wherein $A_1$, m, $R_2$, $R_3$, $R_5$, and x are as defined above.

2. The process of claim 1 wherein said rest-breaking agent is applied in the form of an aqueous solution having a concentration of from 0.1 to 10% of said compound and from 0.5–30% of said rest-breaking agent.

3. The process of claim 2 wherein said compound has a molecular weight of less than 8000 grams/mole.

4. The process of claim 3 wherein said compound is an alkoxylated quaternary ammonium compound represented by the general formula:

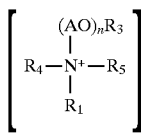

wherein n is an integer from 1 to 50, $X^-$ is an anion, A represents an alkylene group and when n>1, each A may be the same or different alkylene groups, $R_5$ is selected from hydrogen, straight or branched chain alkyl and alkenyl groups having 1–4 carbon atoms, and benzyl, or $R_5X^-$ is carboxymethyl or oxygen; $R_4$ is selected from straight or branched chain alkyl or alkenyl groups having 8 to 22 carbon atoms or a group represented by the formula:

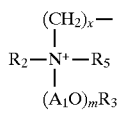

wherein m is an integer from 1 to 50, $R_5$ is as defined above, $A_1$ represents an alkylene group and when n>1, each $A_1$ may be the same or different alkylene groups, x is an integer from 1 to 6, $R_2$ is selected from straight or branched chain alkyl or alkenyl groups having 8–22 carbon atoms; and $R_1$ is selected from hydrogen, straight or branched chain alkyl or alkenyl groups having 1 to 22 carbon atoms, a group represented by the formula:

wherein n' is an integer from 1 to 50 and $A_2$ represents an alkylene group; when n'>1 each $A_2$ may be the same or different alkylene groups, and $R_3$ is selected from hydrogen, straight or branched chain alkyl or alkenyl groups having 1 to 8 carbon atoms and aryl groups having up to 8 carbon atoms.

5. The process of claim 3 wherein said compound is an alkoxylated amine represented by the following general formula:

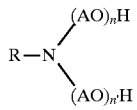

wherein n and n' are integers from 1 to 50, A represents an alkylene group and when n or n' are greater than 1, each A may be the same or different alkylene groups, and R is selected from straight or branched chain alkyl or alkenyl groups having 8 to 22 carbon atoms.

6. The process of claim 5 wherein n>1 and A includes both ethoxy groups and propoxy groups.

7. The process of claim 3 wherein said compound is an alkoxylated amine represented by the following general formula:

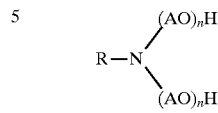

wherein n and n' are integers from 1 to 50, A represents an alkylene group and when n or n' are greater than 1, each A may be the same or different alkylene groups, R is a group represented by the formula:

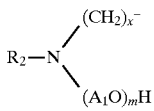

wherein m is an integer from 1 to 50, $A_1$ represents an alkylene group and when m>1, each $A_1$ may be the same or different alkylene groups; x is an integer from 1 to 6, and $R_2$ is selected from straight or branched chain alkyl or alkenyl groups having 8–22 carbon atoms.

8. The process of claim 3 wherein R is selected from alkyl groups having 12–22 carbon atoms.

9. The process of claim 3 wherein said compound is an amine oxide represented by the following general formula:

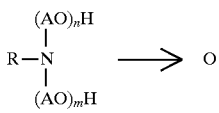

wherein R, A, n and m are as defined in claim 1.

10. The process of claim 1 wherein said plant is selected from the group consisting of grape vines, olive trees, raspberries, strawberries, cranberries, blackberries, loganberries, blackcurrants, redcurrants, almonds, walnuts and chestnuts.

11. The process of claim 1 wherein said rest-breaking compound is selected from the group consisting of hydrogen cyanamide, calcium ammonium nitrate, urea ammonium nitrate, potassium nitrate, the potassium salt of gibberellic acid, kinetin, indoleacetic acid, thiourea, and combinations thereof.

* * * * *